United States Patent [19]

Beckman et al.

[11] Patent Number: 5,277,908
[45] Date of Patent: Jan. 11, 1994

[54] MODIFIED SUPEROXIDE DISMUTASE

[75] Inventors: Joseph S. Beckman; Haralambos Ischiropoulos; Craig D. Smith, all of Birmingham, Ala.

[73] Assignee: The UAB Research Foundation, Birmingham, Ala.

[21] Appl. No.: 892,608

[22] Filed: May 29, 1992

Related U.S. Application Data

[63] Continuation of Ser. No. 613,213, Nov. 14, 1990, abandoned.

[51] Int. Cl.$^5$ .................... A61K 37/50; A61K 37/48; C12N 9/02; C07K 15/00
[52] U.S. Cl. ................. 424/94.4; 424/94.1; 435/189; 530/350; 530/400
[58] Field of Search ................. 424/94.67, 94.4, 94.1, 424/94.5; 530/400, 350; 435/189

[56] References Cited

U.S. PATENT DOCUMENTS

| | | | |
|---|---|---|---|
| 4,656,034 | 4/1987 | Sarnoff | 424/94.5 |
| 4,695,456 | 9/1987 | Wilder | 424/94.5 |
| 4,818,698 | 4/1989 | Sagai et al. | 435/189 |
| 4,842,846 | 6/1989 | Nakano | 424/94.4 |
| 4,968,616 | 11/1990 | Inoue et al. | 435/189 |

OTHER PUBLICATIONS

J. of Biological Chemistry, Hallewell et al., vol. 264, No. 9, Mar. 25, 1989 pp. 5260-5268.
Beyer et al, J. of Biolog, Chem., vol. 262, No. 23, Aug. 15, 1987 pp. 11182-11187.
Yokoyama, et al., "Circulating xanthine oxidase: potential mediator of ischemic injury," American Journal of Physiology 258:G564-570, 1990.
Werns and Lucchesi, "Free radicals and ischemic tissue injury,"*TIPS* 11:161-166, Apr., 1990.
Beckman, et al., "Apparent hydroxyl radical production by peroxynitrite: Implications for endothelial injury from nitric oxide and superoxide," Proc. Natl. Acad. Sci. USA 87:1620-1624, Feb., 1990.
Beckman, "Ischaemic injury mediator," Nature 345:27-28, May 3, 1990.
Greewald, "Superoxide dismutase and catalase as therapeutic agents for human diseases: a critical review," *Free Radical Biology & Medicine* 8:201-209, 1990.
Omar, et al., "Cardioprotection by Cu,Zn-superoxide dismutase is lost at high doses in the reoxygenated heart," *Free Radical Biology & Medicine* 9:465-471, 1990.
Knowles, et al., "Formation of nitric oxide from L-arginine in the central nervous system: A transduction mechanism for stimulation of the soluble guanylate cyclase," *Proc. Natl. Acad. Sci. USA* 86:5159-5162, Jul. 1989.
Hallewell, et al., "Genetically Engineered Polymers of Human CuZn Superoxide Dismutase," *The Journal of Biological Chemistry* 264:5260-5268, Mar. 25, 1989.
Liu, et al., "Polyethylene glycol-conjugated superoxide dismutase and catalase reduce ischemic brain injury," *American Journal of Physiology* 256:H589-593, 1989.
Omar et al., "Protection Afforded by Superoxide Dismutase is Dose Dependent in the in situ Reperfused Rabbit Heart," *Circulation* 80:II-294, Oct., 1989.
Getzoff, et al., "Evolution of CuZn Superoxide Dismutase and the Greek Key β-Barrel Structural Motif," *Proteins: Structure, Function and Genetics* 5:322-336, 1989.

(List continued on next page.)

Primary Examiner—Douglas W. Robinson
Assistant Examiner—Susan M. Weber
Attorney, Agent, or Firm—Needle & Rosenberg

[57] ABSTRACT

A method and compositions for reducing ischemic, inflammatory or septic injury in an animal that includes administration to the animal of an effective amount of a modified superoxide dismutase, wherein the modification comprises substituting a first amino acid residue located within 3-12 Å of the active site of the superoxide dismutase with a second amino acid residue capable of reacting with a highly reactive nitrating species, such as nitronium ion, formed from the reaction of peroxynitrite and superoxide dismutase.

7 Claims, No Drawings

OTHER PUBLICATIONS

Inoue, et al., "Synthesis of a Superoxide Dismutase Derivative that Circulates Bound to Albumin and Accumulates in Tissues Whose pH is Decreased," *Biochemistry* 28:6619–6624, 1989.

Palmer, et al., "Vascular endothelial cells synthesize nitric oxide from L-arginine," *Nature* 333:664–666, Jun. 1988.

Marletta, et al., "Macrophage Oxidation of L-Arginine to Nitrite and Nitrate: Nitric Oxide is an Intermediate," *Biochemistry* 27:8706–8711, 1988.

Parker and Blake, "Crystal Structure of Manganese Superoxide Dismutase from *Bacillus stearothermophilus* at 2.4 A Resolution," *J. Mol. Biol.* 199:649–661, 1988.

Moncada, et al., "Endothelium-derived relaxing factor is identified as nitric oxide," *TIPS* 8:365–368, Oct., 1987.

Hjalmarsson, et al., "Isolation and sequence of complementary DNA encoding human extracellular superoxide dismutase," *Proc. Natl. Acad. Sci. USA* 84:6340–6344, Sep. 1987.

Beyer and Fridovich, "Examination of the Role of Arginine-143 in the Human Copper and Zinc Superoxide Dismutase by Site-specific Mutagenesis," *The Journal of Biological Chemistry* 262:11182–11187, 1987.

Blough and Zafiriou, "Reaction of Superoxide with Nitric Oxide to Form Peroxonitrite in Alkaline Aqueous Solution," *Inorg. Chem.* 24:3502–3504, 1985.

McCord, "Oxygen-Derived Free Radicals in Postischemic Tissue Injury," *Free Radicals and Ischemia* 312:159–163, Jan., 1985.

Stallings, et al., "The Structure of Manganese Superoxide Dismutase from *Thermus thermophilus HB*8 at 2.4-Å Resolution," *The Journal of Biological Chemistry* 260:16424–16432, 1985.

Tainer, et al., "Structure and mechanism of copper, zinc superoxide dismutase," *Nature* 306:284–290, Nov., 1983.

Petrone, et al., "Free radicals and inflammation: Superoxide-dependent activation of a neutrophil chemotactic factor in plasma," *Proc. Natl. Acad. Sci. USA* 77:1159–1163, Feb. 1980.

Pyatak, et al., "Preparation of a Polyethylene Glycol: Superoxide Dismutase Adduct, and an Examination of its Blood Circulation Life and Anti-Inflammatory Activity," *Research Communications in Chemical Pathology and Pharmacology* 29:113–127, Jul. 1980.

Lynch and Fridovich, "Permeation of the Erythrocyte Stroma by Superoxide Radical," *The Journal of Biological Chemistry* 253:4697–4699, Jul., 1978.

Halfpenny and Robinson, "The Nitration and Hydroxylation of Aromatic Compounds by Pernitrous Acid," *J. Chem. Soc.* 939–946, 1952.

MODIFIED SUPEROXIDE DISMUTASE

This application is a continuation of application Ser. No. 07/613,213, filed Nov. 14, 1990, now abandoned.

BACKGROUND OF THE INVENTION

The present invention relates generally to the field of administration of superoxide dismutase (SOD) to reduce ischemic injury or injury following sepsis or inflammation. In particular, this invention relates to a method and compositions for reducing toxic side effects caused by the reaction of SOD and peroxynitrite. Specifically, an effective amount of SOD, modified by substituting amino acid residues close to the active site of the SOD with amino acid residues, such as tyrosine, methionine, or cysteine residues, that can trap the toxic side products of the reaction of SOD with peroxynitrite, such as nitronium ion, is administered to an animal. This invention has particular relevance in the treatment of stroke and head trauma, myocardial ischemia, sepsis, inflammation, adult respiratory distress syndrome, and bronchiopulmonary dysplasia.

Peroxynitrite anion ($ONOO^{3-}$) is a potent oxidant. Peroxynitrite is formed by the reaction of superoxide ($O_2^{3-}$) and nitric oxide in tissues subjected to ischemic, inflammatory or septic conditions. Nitric oxide is present in such tissues. For example, in ischemic injury, ischemia allows calcium entry into endothelial cytoplasm due to failure of ionic pumps and opening of ion channels. Endothelium and neurons produce nitric oxide by an oxygen ($O_2$) dependent calmodulin activated nitric oxide synthetase which oxidizes arginine in the presence of NADPH (Palmer et al., Nature (London) 333:664–666 (1988); Knowles et al., Proc. Natl. Acad. Sci. (USA) 86:5159-62 (1989); Marletta et al., Biochem., 27:8706-8711 (1988)). Reperfusion allows rapid nitric oxide synthesis by providing $O_2$ to the enzyme and other substrates already present as a result of ischemia.

Superoxide is also present in injured tissue. For example, ischemia induces intracellular $O_2$ production by xanthine oxidase, mitochondria and other sources. The $O_2$ can escape into the extracellular millieu through anion channels (Lynch et al., J. Biol. Chem., 253: 4697-4699 (1978)). Extracellular $O_2^-$ and nitric oxide are also produced in the vascular lumen by activated neutrophils and macrophages, and by circulating xanthine oxidase released from liver (Yokoyama et al., Amer. J. Physiol., 258:G564–G570 (1990); Moncada et al., Biochem. Pharmacol., 38:1709–1715 (1989)). The superoxide radical is also an important mediator of both the inflammatory response of neutrophils and of the damage that occurs during reperfusion of anoxic tissue after organ transplantation or when a blood clot is removed. (Petrone et al., Proc. Natl. Acad. Sci (USA), 77:1159-163 (1980)).

NO reacts rapidly with $O_2^-$ both intracellularly and in the vascular lumen to form peroxynitrite (Blough et al., Inorg. Chem., 24:3504-3505 (1985); Beckman et al., Proc. Natl. Acad. Sci. (USA), 87:1620-1624 (1990)). The rate of peroxynitrite formation depends upon $O_2^-$ and nitric oxide concentrations. Peroxynitrite can be toxic by at least three mechanisms: hydrogen ion-catalyzed homolytic cleavage to form hydroxyl radical (•OH) and nitrogen dioxide ($NO_2$), direct reaction with sulfhydryl groups, and reactions with SOD and transition metals to form hydroxyl ion ($^-OH$) and nitronium ion ($NO_2^+$) a potent nitrating agent (Beckman et al., Nature (London) 345:27-28 (1990)). Thus, peroxynitrite is a reactive species which can produce other highly reactive species such as •OH, $NO_2$, and $NO_2^+$.

Superoxide dismutases consist of several distinct families of metal-containing enzymes that catalyze the dismutation of the oxygen radical superoxide by the following two step reaction:

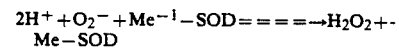

where Me refers to the metal bound in the active site. This metal undergoes repeated cycles of oxidation and reduction in the reactions given above. Many compounds can either reduce or oxidize superoxide, but the distinguishing feature of a superoxide dismutase is the catalysis of both reactions given above. A series of positively charged amino acids positioned near the active site of the SODs generates an electrostatic gradient which attracts the negatively charged $O_2^-$ into the active site.

Three families of SODs are distinguished by the metal in the active site: the copper+zinc (Cu,Zn) SOD family, the manganese (Mn) SOD family and the iron (Fe) SOD family. The vast majority of therapeutic studies have been performed using Cu,Zn SODs, which naturally occur in the cytoplasm of eukaryotic cells as a dimer of two identical 16 Kd peptides. There is also a distinct Cu,Zn SOD found in plasma, which is a tetramer. Another form of SOD contains manganese (Mn) and is found in mitochondria. This protein has an amino acid sequence distinct from the Cu,Zn SOD but is similar to the sequence for Mn and Fe SODs found in bacteria.

SOD's have been commonly utilized to prevent or reduce oxidation injury in the treatment of stroke and head trauma, myocardial ischemia, abdominal vascular occlusion, cystitis, and a variety of inflammatory conditions (Greenwald, Free Radical Biol. and Med., 8:201-209 (1990); McCord, New Eng. J. Med., 312:159-183 (1985); U.S. Pat. No. 4,695,456; U.S. Pat. No. 4,656,034).

However, there have been several disappointing results in humans treated with native human Cu,Zn SOD. One explanation for these results may be that the native enzyme has a circulatory half life of only minutes because of rapid clearance by the kidneys (Petkau et al., Res. Commun. Chem. Pathol. Pharmacol., 15:641-657 (1976)).

To address this problem, several longer-lived derivatives of SODs have been developed. Human Mn SOD has been cloned and human trials have been reported by Nimrod et al., in Medical Biochem. and Chem. Aspects of Free Radicals, N.Y.: Elsevier Science Pub., 743-746 (1989). Genetic engineering has produced a long-lived modification of human cytoplasmic Cu,Zn SOD (Hallewell et al., J. Biol. Chem., 264:5260-5268 (1989)). Other modifications, such as polyethylene glycol conjugates of both human and bovine Cu,Zn SOD have longer half lives and are less immunogenic than unmodified forms (Pyatak et al., Res. Commun. Chem. Pathol. Pharmacol., 29:113-127 (1980); Saifer et al., Proc. Fifth Internatl. Conf. on Suoeroxide and Suoeroxide Dismutase (Jerusalem) (1989)).

Another problem with in vivo SOD therapy has recently been reported in which treatment with higher SOD dosage levels to reduce ischemic injury resulted in an increased infarct size (Omar et al., *Circulation* 80:SII-294 (1989); Werns et al., *Tr. Pharmacol. Sci.*, 1:161–166 (1988)). Further, the use of SOD in tissues containing $ONOO^-$ can lead to the production of other destructive species, such as $NO_2^+$. Thus, there exists a need for an improved therapy to treat ischemic, inflammatory or septic conditions.

SUMMARY OF THE INVENTION

The above deficiencies in the prior art are solved by the present invention, which provides for an improved superoxide dismutase therapy. This invention comprises a method and composition for reducing ischemic injury, or injury associated with sepsis or inflammation, by reducing the toxic side effects caused by the reaction of SOD and peroxynitrite. A SOD is modified either chemically or by site-directed mutagenesis, by substituting at least one amino acid residue close to the active site of SOD, particularly close to the rim around the active site, most particularly within 3–12 Å of the active site, with an amino acid residue, such as a tyrosine, a methionine residue or cysteine residue, that can trap the toxic side products, such as $NO_2^+$, of the reaction of SOD with peroxynitrite. An effective amount of modified SOD is administered, such as parenterally, particularly intravenously, intraarticularly, intramuscularly, or subcutaneously, or by intratracheal infusion, inhalation, or intranasally to an animal to treat ischemic, inflammatory or septic conditions, such as stroke, head trauma, or arthritis. Such effective amount preferably ranges from 100 to 10,000 units of activity/kilogram of body weight, and more preferably ranges from 1000 to 10,000 units of activity/kilogram of body weight.

Therefore, it is an object of this invention to provide a means for protecting tissue from oxidative damage associated with ischemia, sepsis and inflammation. It is a further object of this invention to prevent injury to tissue caused by toxic side reactions of superoxide dismutase.

Furthermore, an objective of this invention is to provide a method and compositions that reduce the injury or side effects associated with treatment therapy utilizing SOD. It is a particular object of this invention to provide a SOD that is modified so as to trap the toxic products formed in vivo upon treatment with SOD. In addition, it is an object of this invention to provide for a SOD that is modified by replacing at least one amino acid residue close to the active site of SOD with an amino acid residue that can trap the toxic side products formed during SOD therapy. It is a further object of this invention to provide a method for treating ischemic, inflammatory or septic conditions comprising administering the modified SOD to an animal.

These and other objects and advantages of this invention are described in the following detailed description, which is not meant to be limiting.

DETAILED DESCRIPTION

Although SODs comprise a family of several distinct enzymes that vary in amino acid sequence, their catalytic mechanisms are very similar. Thus, the tertiary structure surrounding the active sites of the various SODs are sufficiently homologous to permit effective modification by the same or very similar methods.

For example, all Cu,Zn superoxide dismutase molecules are dimers of identical subunits and each subunit contains about 153 amino acids (depending on the species) and one copper ion and one zinc ion. The crystallographic structure of bovine Cu,Zn superoxide dismutase, refined to a resolution of 2.0 Å, shows that the structural core of the subunit is a flattened Greek key β-barrel motif consisting of eight antiparallel beta-strands joined by seven turns or loops. The catalytic copper ion is ligated to the surface of the β-barrel by four histidine residues and occurs at the base of a channel formed by two loops extending from the β-barrel. In addition to forming the superoxide channel, the two loops encode specific functional subdomains involved in pre-collision electrostatic guidance of substrate (loop VII), zinc binding (loop IV), and dimer contact (loop V) (Getzoff et al., *Nature*, 306:287–290 (1983)).

Superoxide is drawn into the active site by electrostatic fields generated by the spatial arrangement of positively charged amino acids forming a ring near the active site and negatively charged amino acids more distant from the active site. This tends to draw the negatively charged superoxide into the active site and accelerates the reaction rate to near the theoretical diffusion limit.

Generally, the catalytic mechanism of SODs involve two sequential reactions. First, one molecule of superoxide transfers an electron to the metal in the active site of SOD and is released as oxygen. A second superoxide entering the active site of SOD picks up the electron from the metal, thereby becoming reduced to hydrogen peroxide while regenerating native SOD. Coordination of the metal in the SOD protein alters the redox potential favoring the repeated reduction and oxidation by superoxide. For example, the midpoint potential of Cu in Cu,Zn SOD is about 0.4 volts, and undergoes the following reactions:

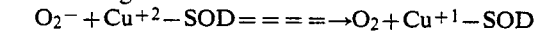

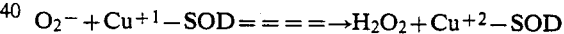

Peroxynitrite also reacts with the active site of SOD to produce $NO_2^+$, which is a highly reactive species that can cause considerable physical damage in vivo and may account for the apparent toxicity of SOD in high doses to ischemic heart. Peroxynitrite also is attracted to the active site by the same electrostatic field that draws $O_2^-$ into the active site (Getzoff et al., *Nature*, 306:287–290 (1983); Tainer et al., *Mol. Biol.*, 160:181–217 (1982)). The O—O part of peroxynitrite will fit into the hydrophobic pocket of the active site, while $NO_2^-$ extends into the solvent space.

Cu,Zn SODs catalyze the decomposition of $ONOO^-$ to produce $NO_2^+$ and $OH^-$ from peroxynitrite with copper playing an essential role in this reaction. Once in the active site, $^-OONO$ decomposes to give $OH^-$ and the nitronium ion ($NO_2^+$), apparently by forming a transient cuprous adduct as shown:

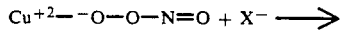

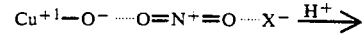

$$Cu^{+2} + {}^-OH + NO_2^+ \cdots X^I$$

The nitronium ion, which has a high heat of formation, might be transiently stabilized as a salt, such as by complexing with phosphate or chloride anion ($X^-$). The positively charged nitronium ion will be repelled by the same electrical field that drew $ONOO^-$ into the active site, arcing towards the negatively charged distal regions where the sole tyrosine is located. This positioning allows $NO_2^+$ to nitrate the tyrosine residue to form 3-nitrotyrosine similar to the well-known nitronium ion displacement of hydrogen ion from the ring of tyrosine to form 3-nitrotyrosine. The $X^-$ may serve as a carrier anion for the nitronium ion in aqueous solutions, allowing it to exist long enough in aqueous solution to nitrate tyrosine.

Evidence that SOD produces $NO_2^+$ when it reacts with peroxynitrite is verified by the isolation of a stable yellow adduct, which is formed when peroxynitrite is added to a solution of bovine Cu,Zn SOD. As discussed below, the yellow adduct corresponds to the formation of 3-nitrotyrosine on the tyrosine residue of SOD. The yellow adduct is typical of nitrated phenols such as p-nitrophenol (Halfpenny et al., *J. Chem. Soc.*, 1952:939–946 (1952)). Furthermore, SOD catalyzes the nitration of other phenols as well as tyrosines on other proteins at a rate which could be biologically significant.

Evidence for SOD-Catalyzed Nitration of SOD and Phenolics

The yellow adduct produced from bovine Cu,Zn SOD reacting with $ONOO^-$ was crystallized and used to derive the x-ray structure. Electron density maps calculated from x-ray diffraction from these crystals show an increase in electron density near the ortho position of the sole tyrosine residue 108 on the bovine Cu,Zn SOD, indicating that 3-nitrotyrosine is formed. This position is located between 18–21 Å from the active site on the same subunit and considerably further from the opposing subunit of the dimer, indicating that the positively charged nitronium ion was formed in the SOD active site and then directed to the distal tyrosine by the electrostatic fields generated from charged amino acids that form a rim around the active site of SOD.

The pH-dependent spectra of the SOD-peroxynitrite adduct are also consistent with formation of 3-nitrotyrosine, exhibiting a $pK_a$ of 7.6 between an absorbance maximum in the alkaline range at 438 nm ($E = 4,600$ $M^{-1}cm^{-1}$) and an absorbance maximum at pH 6.0 of 356 nm ($E_{356}$ nm $= 3,500$ $M^{-1}cm^{-1}$). Similar spectra are obtained by treating native SOD with tetranitromethane, which is a standard reagent used by protein chemists to produce 3-nitrotyrosine in proteins. The $pK_a$ of 3-nitrotyrosine is near 7.0 with $E_{350}$ nm $= 3,400$ $M^{-1}cm^{-1}$ in acid and $E_{438}$ nm $= 4,200$ $M^{-1}cm^{-1}$ in alkali. The SOD--OONO adduct maxima at 350 and 438 nm are lost with reduction by dithionite (sodium hydrosulfide), but not ascorbate, glutathione or borohydride. This is consistent with the established reaction of dithionite reducing 3-nitrotyrosine to a colorless amine. Laser Raman spectra of the peroxynitrite-treated SOD are nearly identical to authentic 3-nitrotyrosine. The only subtle differences between the spectra are a broadening of a major peak at 1340 $cm^{-1}$ and the splitting of a minor peak at 830 $cm^{-1}$, both of which are consistent with the restricted rotation of 3-nitrotyrosine constrained within the SOD protein.

The reaction of peroxynitrite with Cu,Zn SOD also produces a series of increasingly negatively charged SOD variants on native polyacrylamide gel electrophoresis, indicative of 2–5 additional negative charges being present on the protein. Thus, multiple sites on SOD are modified during the reaction with peroxynitrite, suggesting that the formation of nitrotyrosine is simply the most visible of several changes to the SOD protein. The number of peroxynitrite-mediated modifications to SOD could be reduced in a concentration-dependent manner by either phenol or the tyrosine-containing protein lysozyme. Evidence is presented below that both phenol and lysozyme are also nitrated. Thus, the self-nitration of SOD involves a process that is competitively inhibited by adding exogenous phenolic compounds.

SOD also catalyzes the nitration of a wide range of phenolic compounds, including tyrosines, in other proteins like egg white lysozyme. HPLC analysis of the products from the SOD-catalyzed reaction of $ONOO^-$ with 1 mM phenol yields both 2- and 4-nitrophenol but no biphenol. The increase in phenol nitration measured by HPLC was linearly related to SOD concentration.

The rate of phenol nitration by peroxynitrite in the presence of Cu,Zn SOD can be measured by stopped flow spectroscopy at 412 nm. At moderately alkaline pH (between pH 8–10), the kinetics of SOD catalyzed nitration are relatively simple to interpret because peroxynitrite decomposes slowly, the phenol nitration products have larger extinction coefficients, and the spontaneous rate of phenol nitration by proton-catalyzed decomposition of $ONOO^-$ is greatly reduced. The rate of absorbance increase at 412 nm was linear for the first 3–5 seconds at pH 9 and directly proportional to SOD concentration. At pH 9, a minimum estimate for the apparent second order rate constant for phenol nitration by SOD and ONOO. is approximately $10^5$ $M^{-1}s^{-1}$. This rate is about $10^4$ fold slower than the reaction with $O_2^-$, but demonstrates that the peroxynitrite reaction proceeds at a significant rate.

The Mn SOD catalyzes the nitration of phenol much like Cu,Zn SODs. Several tyrosines are present on the Mn SOD; at least 3–4 of the 7 tyrosines are also nitrated when the enzyme is treated with peroxynitrite in the absence of phenol. Unlike the Cu,Zn SOD, the Mn SOD is inactivated by large concentrations of peroxynitrite. If the Mn SOD is first treated with 15 mM peroxynitrite at pH 7.8, catalytic activities are lost for both the superoxide and peroxynitrite reactions. An essential tyrosine near the active site (tyrosine 34 in the bacterial sequences; tyrosine 58 in the human sequence) of Mn SOD is slowly being modified by a small percentage of enzyme turnover rate (Stallings et al., *J. Biol. Chem.* 260:16424–16432 (1989). This suggests that substituting an amino acid to place tyrosine near the active site at some other position could be effective. Thus, improvements by the addition of sulfhydryl groups or tyrosine near the active site could be made on both the Mn and Cu,Zn SOD.

The Cu,Zn SOD--OONO adduct had normal catalytic activity when measured by a standard SOD assay employing inhibition of cytochrome c reduction by xanthine oxidase (McCord et al., *J. Biol. Chem.*, 244:6049–6055 (1969), suggesting that the $-OONO$ does not remain bound in the active site. However, 3-nitrotyrosine has a $pK_a$ near 7.5 and the resulting negative charge in the active site could reduce the activity of SOD for both superoxide and peroxynitrite. Copper in the SOD active site is necessary for the formation of the adduct, as evidenced by the lack of nitration of 1 mM phenol by 2.0 mg/ml Cu-free SOD with 1 mM $^-$OONO at pH 7.4. The Cu-free SOD can be obtained by reversible removal of copper with KCN; this type of metal replacement experiment with Cu,Zn SOD has been performed frequently over the past twenty years. Following use of a slightly modified procedure developed by Rotili et al., in which the copper is removed by reduction with borohydride followed by dialysis against 50 mM KCN, the Zn-containing apoprotein does not form the characteristic 3-nitrotyrosine when peroxynitrite is added. This is evidenced by the absence of a large peak of absorbance at 412 nm. Replacement of copper at the active site restored normal enzymatic activity for both $O_2^-$ and $ONOO^-$. Cyanide is also a weak inhibitor of Cu,Zn SOD and also inhibits SOD-catalyzed nitration by peroxynitrite. These results show that SOD-catalyzes nitration by peroxynitrite.

Evidence Against a Free Radical Mechanism of Nitration

A potential nitration mechanism might involve the formation of nitrogen dioxide (NO$_2$) catalyzed by SOD or SOD may catalyze the formation of a strong oxidant, like hydroxyl radical, as well as nitrogen dioxide. We could find no evidence to support either of these two mechanisms to explain the SOD-catalyzed nitration of a phenolic ring.

The nitration reaction with SOD was specific for ONOO$^-$, as evidenced by little or no complex formation from treating either reduced or oxidized SOD with up to 4 mM nitric oxide, NO$_2$ NO$_2^-$ or NO$_3^-$. Furthermore, only 0.29±0.09 μM NO$_2$ was formed by SOD reacting with 1000 μM ONOO$^-$. Also, addition of 100 mM dimethylsulfoxide to trap any hydroxyl radical formed by decomposition of ONOOH increased NO$_2$ by 250 fold without affecting the amount of phenol nitration catalyzed by SOD. However, the background level of nitration was greater in the presence of DMSO without SOD. Finally, nitration by NO$_2$ proceeds through phenyl radical intermediates and produces significant amounts of biphenols. We could detect no biphenol formation by HPLC from phenol nitration by SOD plus peroxynitrite at alkaline pH (pH>7.5). At neutral to acidic pH, some biphenyl formation takes place by the proton-catalyzed decomposition of peroxynitrite, which forms •HO and NO$_2$ as intermediates.

Preparation of Modified SODs

As discussed above, SOD can react with ONOO$^-$ producing toxic side products. This invention is designed to render these products, particularly NO$_2^+$, less harmful by modifying the SOD to react with the toxic side product. For instance, SOD can be modified to position a tyrosine residue near the active site so that the NO$_2^+$ that is produced will nitrate the tyrosine, thereby eliminating the toxic NO$_2^+$ species.

It is desirable to position a tyrosine residue near the active site where the ortho position of the tyrosine ring can interact with the ONOO$^-$ moiety. When peroxynitrite reacts with the copper in the active site to form nitronium ion, the nitronium ion will attack the phenolic ring of tyrosine to form 3-nitrotyrosine rather than being released into solution.

Also, by positioning the nucleophilic sulfur of cysteine or methionine residues near the active site, one may effect a trap for nitronium ion or peroxynitrite. The intermediate nitrothiol will be unstable and may be able to regenerate the sulfhydryl group with a spontaneous reaction with low molecular weight thiols.

Peroxynitrite anion reacts rapidly with sulfhydryl groups, most likely according to the following series of reactions:

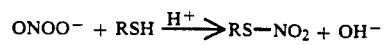

The resulting sulfonic acid may be regenerated to a sulfhydryl group by reaction with glutathione or other thiol agents as follows:

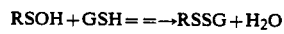

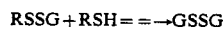

where GSH is glutathione or some other low molecular weight sulfhydryl agent.

Several threonines exist in or near the active site of Cu,Zn SOD, which could be substituted with a cysteine residue with minor effects upon structure. A limitation to cysteine substitutions is that the SH group is susceptible to autoxidation or may be oxidized during the catalytic cycle of superoxide.

Substitution of a methionine residue near the active site may be more useful. The sulfur of methionine should be far less susceptible to autoxidation, but is still highly nucleophilic and susceptible to attack by nitronium or peroxynitrite. Methionine is slightly larger and more hydrophobic than cysteine, imposing greater constraints upon where methionine may be substituted on the protein.

Preparation of Site Directed Mutants

The preparation of site directed mutants is a standard procedure. For example, basic procedures for the preparation of site-direct mutants near the active site of human Cu,Zn SOD is similar to that used by Beyer et al (Beyer et al., *J. Biol. Chem.*, 282:11182–11187 (1987)). DNA manipulations are performed using standard conditions as described by Maniatis et al. (Cold Springs Harbor Laboratory, Cold Springs Harbor, N.Y., (1982)). For example, in preparing modified human cytoplasmic Cu,Zn SOD, a 1.8 Kbp BamHI DNA fragment containing the wild type HSOD (human Cu,Zn SOD sequence) is subcloned in M13 (mp10) and a single stranded template DNA is prepared containing the coding strand of HSOD. Mutagenic oligonucleotide primers containing the appropriate anticodon for the desired amino acid substitution are synthesized with an automated DNA synthesizer (such as the Chiron Gene-O-Matic) using standard phosphoramidite synthetic techniques. The mutagenic oligonucleotide primer is constructed to contain 8–15 bp of the matching sequences for HSOD on both sides of the mutated sequence. The mutagenic oligonucleotide is then hybridized to the single strand M13 DNA containing the HSOD fragment and a covalently closed double stranded DNA is synthesized by primer extension. Mutant plaques from *E. coli* JM101 transformed with the M13 virus are identified using the radiolabeled mutagenic oligonucleotide as a hybridization probe and then confirmed by DNA sequencing. Double stranded DNA is prepared from the sequenced isolates and digested with NcoI and SalI to isolate a 520 bp fragment containing the HSOD cDNA, which is purified by PAGE electrophoresis. This purified fragment is cloned into the yeast expression plasmid (pCl/1PGAPSOD) containing the glyceraldehyde phosphate dehydrogenase gene 49 promotor as described by Maniatis et al.

Yeast strain AB110 is transformed with Pcl/1PGAP-SOD and the corresponding mutated plasmid. Transformed colonies are selected on agar plates lacking leucine. These colonies are then used to inoculate larger fermentation flasks in nonselective YEPD media supplemented with 3 mM $CuSO_4$, and the final cultures are lysed with glass beads. The Cu,Zn SOD is isolated by ammonium sulfate precipitation and DEAE chromatography as described by Beyer et al above.

The mutated HSOD may also be expressed in *E. coli* for the initial screening of mutations to select the best scavenger of peroxynitrite. For human usage, the final product is prepared from yeast to avoid endotoxin contamination from the bacterial coat.

The DNA sequences encoding both human Mn SOD and extracellular Cu,Zn SODs have been cloned. With slight changes in the restriction nucleases used to excise the initial DNA fragment to be mutated, the procedures given above are readily adaptable to generate desired site-directed mutants for all SODs. To express the Mn SOD, Mn will be added to the culture medium.

Chemical Preparation of Modified SODs

The artificial construction of a tyrosine-like residue may also be accomplished by direct chemical modification. This is a standard modification performed by protein chemists and involves adding a phenolic group to the $\epsilon$-amino group of lysine with the Hunter-Bolton reagent (Thompson et al., *Biochem.*, 26:743-750 (1987)). This procedure is frequently utilized to radiolabel small peptides by reacting the phenolic ring with $^{125}I$. Cu,Zn SOD contains approximately 19 free amino groups, many of which are clustered near the active site to create an electrostatic field drawing the negatively charged superoxide and peroxynitrite anions into the active site. Thus, it may be possible to use a simple chemical reaction to place several phenolic rings near the active site. A major limitation of direct chemical modification is that multiple sites on the protein may undergo modification, which can reduce enzymatic activity or create new antigenic sites.

Amino Acid Substitutions

For cytoplasmic and extracellular human SODs, all amino acid residues within 12 Å of the copper center are suitable candidates for substitution with tyrosine, cysteine or methionine residues. The distances from the copper to these residues varies from 5 to 10.7 Å. The preferred amino acid candidates for substitution in the human cytoplasmic Cu,Zn SOD are residues 132-142, which form a loop or rim around the active site. The equivalent positions for the human extracellular Cu,Zn SOD are residues 172-185. Residue 48, which is a phenylalanine, may be modified to a tyrosine. Threonine 58, alanine 60 to proline 62 and comprise part of the active site. Threonine 58, alanine 60, and glutamine 165 could be replaced by cysteine or methionine; arginine 143 is also a good candidate for substitution.

In bovine Cu,Zn SOD, the amino acids number 56, 58 to 60, 63, 131 and 134 to 140 form a rim around the active site that could be modified without necessarily disrupting the binding site for superoxide. Residue 135 is a threonine that is only 5.3 Å from the copper and might be substituted with a cysteine. Residue 48 is a phenylalanine which could be changed to a tyrosine with minimal affects upon structure, but it is somewhat removed from the active site. The amino terminal lysine 151 of the other monomer is close enough to the active site that it may also be modified.

The human extracellular SOD is closely related to the cytoplasmic enzymes (Hjalmarsson et al., *Proc. Natl. Acad. Sci.*, 84:6340-6344 (1987)), except for the presence of an extensive amino terminal tail that is probably needed for assembly of the tetramer and a carboxy-terminal sequence responsible for binding the extracellular SOD to heparin-sulfate groups present on endothelial cell surfaces. The positions listed for the extracellular SOD are inferred from analogy to the bovine cytoplasmic SOD sequence, which seems reasonable because of the high sequence homology in the active site region.

The following amino acid substitutions for Mn SOD were determined by homology to the Bacillus stearothermophilus and consideration of the x-ray structure (Parker et al., *J. Mol. Biol.*, 199:649-661 (1988)) The numbering refers to the human liver Mn-SOD with the N-terminal signal sequence. The active site region consists of part of the first alpha-helix ($\alpha$1) from leucine 49 to glutamine 59. This region lines one side of the active site and is the most likely path for superoxide entering the active site. The sequence from alanine 96 to phenylalanine 101 of the third alpha helix ($\alpha$3) lines the opposite side of the active site but is slightly deeper and forms the pocket near the superoxide binding site. A fold in the sequence from serine 139 to serine 146 joins the fifth alpha helix ($\alpha$5) to the tail of beta sheet ($\beta$1) and forms another part of the active site. The sequence from cysteine 164 to leucine 170 forms a bend between the head of beta sheet ($\beta$2) leading to the tail of $\beta$3. Glutamine 166 in this sequence is important for hydrogen bonding to tyrosine 58. The final sequence contributing to the active site is from valine 184 to glutamine 192, which is highly conserved in all species.

Testing of Site-Directed Mutants

Once the site-directed mutants of SOD are purified, a sample is treated with peroxynitrite to test whether the mutant SOD is inactivated. The catalytic activity for the superoxide dismutase is determined by the standard assay of inhibition-of-cytochrome c-reduction by xanthine oxidase before and after treatment with peroxynitrite. The rate of phenol nitration by peroxynitrite is also determined by stopped flow spectroscopy, monitoring the absorbance increase at 412 nm. For the wild-type SOD, phenol nitration is linear for the first 2-6 seconds, depending upon the assay pH. A nonlinear decrease in the rate of phenol nitration is indicative of progressive inactivation of the SOD. From these data, the reaction rates are calculated for superoxide dismutation, peroxynitrite-mediated nitration and inactivation of SOD by peroxynitrite for each mutant SOD. The mutants that retain high superoxide dismutation activity and low rates of phenol nitration are selected for further animal experimentation to determine their efficacy at reducing ischemic injury. In particular, we use a highly reproducible surgical procedure to induce a stroke in rats and measure the reduction of infarct volume (dead brain tissue) as a measure of efficacy. This procedure comprises occlusion of the middle cerebral artery and a ninety-minute occlusion of the common carotid artery followed by reperfusion for 24 hours (Liu et al., *Am. J. Physiol.*, 256:H589-H593 (1989). An effective dose of modified SOD is administered to the animal for treatment of ischemic, inflammatory or septic conditions. Such administration may be accomplished by any effective route, preferably parenterally, such as intravenously, intraarticularly, intramuscularly or subcutaneously, or by intratracheal infusion, inhalation or intranasally. An effective dose preferably ranges from 100 to 10,000 units of activity/kilogram of body weight, and more preferably ranges from 1000 to 10,000 units of activity/kilogram of body weight. The relevant dosage rate depends on the particular symptom or organ being treated.

An important modification of the Cu,Zn SOD has been to bind 5-17 molecules of polyethylene glycol (PEG) ($-O-(CH_2-CH_2-O)_n-CH_3$) to lysine on the SOD surface. PEG is an ideal polymer because it has little or no toxicity or reactivity. The PEG modification of proteins reduces immunogenicity, increases circulatory half-life from a few minutes to an upper limit of 7 days in humans, and can increase cell association to cultured endothelial cells. An appropriate PEG modification of SOD will most likely continue to be appropriate for a therapeutically useful SOD.

What is claimed is:

1. A modified superoxide dismutase, which reacts with a highly reactive nitrating species formed from the reaction of peroxynitrite and superoxide dismutase and is useful for treating inflammation, sepsis, ischemia and reperfusion injury, comprising a superoxide dismutase, wherein the superoxide dismutase has been modified by substituting an amino acid residue selected from the group consisting of tyrosine, methionine and cysteine for an amino acid residue other than tyrosine, methionine and cysteine which is located with 3-12 Å of the catalytic metal of the active site of the superoxide dismutase.

2. The modified superoxide dismutase of claim 1, wherein the highly reactive nitrating species is nitronium ion.

3. The modified superoxide dismutase of claim 1, wherein the superoxide dismutase is a Cu,Zn superoxide dismutase derived from the cytoplasm of eukaryotic cells.

4. The modified superoxide dismutase of claim 1, wherein the superoxide dismutase is a Cu,Zn superoxide dismutase derived from plasma.

5. The modified superoxide dismutase of claim 1, wherein the superoxide dismutase is a Mn superoxide dismutase derived from mitochondria.

6. The modified superoxide dismutase of claim 3, wherein the Cu,Zn superoxide dismutase is bovine Cu,Zn superoxide dismutase.

7. The modified superoxide of claim 3, wherein the Cu,Zn superoxide dismutase is human Cu,Zn superoxide dismutase.

* * * * *